(12) United States Patent
Rhee et al.

(10) Patent No.: US 8,574,921 B2
(45) Date of Patent: Nov. 5, 2013

(54) OPTICAL SENSING MEMBRANES, DEVICES AND METHODS FOR SIMULTANEOUS DETECTION OF TWO OR MORE PARAMETERS OF DISSOLVED OXYGEN CONCENTRATION, PH AND TEMPERATURE

(75) Inventors: Jong Il Rhee, Gwangju (KR); Chun-Kwang Kim, Daejeon (KR); Ok-Jae Sohn, Daejeon (KR)

(73) Assignee: Industry Foundation of Chonnam National University (KR)

( * ) Notice: Subject to any disclaimer, the term of this patent is extended or adjusted under 35 U.S.C. 154(b) by 511 days.

(21) Appl. No.: 12/432,175

(22) Filed: Apr. 29, 2009

(65) Prior Publication Data
US 2010/0279428 A1    Nov. 4, 2010

(51) Int. Cl.
*G01N 21/76* (2006.01)
(52) U.S. Cl.
USPC ............ 436/172; 436/68; 436/74; 436/96; 436/163; 422/82.05; 422/82.07; 422/82.08
(58) Field of Classification Search
None
See application file for complete search history.

(56) References Cited

U.S. PATENT DOCUMENTS 6,379,969 B1 * 4/2002 Mauze et al. .............. 436/68

OTHER PUBLICATIONS

Dong, Hanjiang, et al., Sol-gel polycondensation of methyltrimethoxysilane in ethanol studied by 29Si NMR spectroscopy using a two-step acid/base procedure, 2007, Journal of Sol-Gel Science Technology, vol. 41, pp. 11-17.*
P.A.S. Jorge et al., Dual sensing of oxygen and temperature using quantum dots and a ruthenium complex, Analytica Chimica Acta 606, 2008, pp. 223-229.
Ganna S. Vasylevska et al., Indicator-Loaded Permeation-Selective Microbeads for Use in Fiber Optic Simultaneous Sensing of pH and Dissolved Oxygen, Chemical Material, 2006, vol. 18, pp. 4609-4616.
Yining Shi et al., Dual-analyte spectroscopic sensing in sol-gel derived polyelectrolyte-silica composite thin films, Talanta, 1998, vol. 47, pp. 1071-1076.

* cited by examiner

*Primary Examiner* — Robert Xu
(74) *Attorney, Agent, or Firm* — Cantor Colburn LLP

(57) ABSTRACT

Provided is an optical sensing membrane, including a mixture of two or more fluorescent dyes for detection of dissolved oxygen concentration, pH and temperature, immobilized on a support, a detection device including the optical sensing membrane and a detection method using the detection device.

7 Claims, 4 Drawing Sheets

Ex 420 / Em 520  gain : 50

[R: Rudpp, H: HPTS]

OPTICAL SENSING MEMBRANES, DEVICES AND METHODS FOR SIMULTANEOUS DETECTION OF TWO OR MORE PARAMETERS OF DISSOLVED OXYGEN CONCENTRATION, PH AND TEMPERATURE

BACKGROUND OF THE INVENTION

1. Field of the Invention

The present invention relates to simultaneous optical detection of two or more parameters of dissolved oxygen concentration, pH and temperature and, more particularly, to an optical sensing membrane, comprising a mixture containing two or more fluorescent dyes for detection of dissolved oxygen concentration, pH and temperature, immobilized on a support, a detection device including the optical sensing membrane, and a detection method using the detection device.

2. Description of Related Art

Dissolved oxygen concentration, temperature and pH are important parameters in fields of environmental monitoring, ocean research, food industries, bioengineering, and medicines. Optical detection has an advantage over other methods since it can be carried out in a non-invasive manner, through a bioreactor or a reaction vessel of glass. In this case, sensing materials are positioned on an inner wall of the reaction vessel and detection is carried out by reflection or fluorescence in the outside of the reaction vessel. Further, the optical sensor has another advantage not to have electromagnetic fields generated since it measures signals using the light instead of electronic element and transfers the measured information using the light. In particular, it is widely used in various fields of sensors due to development of optical dyes selectively emitting the light depending upon specific materials, e.g., dissolved oxygen molecules, carbon dioxide molecules, and the like, and pH variance. Such optical analysis is widely used in various fields since it meets economic factors such as time and cost reduction. Recently, a compact multiple bioreactor has been actively developed using a compact reactor and an optical monitoring technique. The compact multi-bioreactor has an advantage of minimizing costs for process development, since it enables the development of desired process conditions at low costs for a short period of time in the optimization of production process of pharmaceuticals and biotechnological products.

Fluorescent dyes capable of sensing dissolved oxygen concentration, pH and temperature include Rudpp (tris-4,7-dipenyl-1,10-phenanthroline) ruthenium (II) complex, HPTS (8-hydroxypyrene-1,3,6-trisulfonic acid trisodium salt), Quantum dots (Qds) and rhodamine B. Rudpp has a property of emitting fluorescence of 600 nm when an excitation light of 480 nm is incident, in which the fluorescence is generated in inverse proportional to dissolved oxygen concentration. HPTS has a property of emitting fluorescence of 520 nm when an excitation light of 410 nm is incident, in which the fluorescence intensity is increased as a hydrogen ion concentration is decreased. Quantum dots and rhodamine B are used as fluorescent dyes for measuring temperature.

Simultaneous detection of two or more of dissolved oxygen concentration, pH and temperature is required in a complicated cultivation and process. Further, since a quenching effect of dissolved oxygen concentration is greatly influenced by temperature, it is important to know temperature in the optical detection of dissolved oxygen concentration. Recently, fluorescent dyes for simultaneous optical detection of two parameters have been reported. For example, "Talanta 47 (1998) pp. 1071-1076" describes a technique of immobilizing ferrozine, an iron indicator, and HPTS, a pH indicator, in adjacent areas of a single thin membrane, to detect iron and pH in two distinguishable wavelengths by attenuated total reflection (ATR) spectroscopy. "Chem. Mater. 2006 pp. 4609-4616" describes a single-fiber optical sensor capable of simultaneously detecting pH and dissolved oxygen concentration, which has carboxyfluorescein as a pH probe and Rudpp as a dissolved oxygen probe, respectively. However, they have never disclosed the combination of two or more fluorescent dyes of Rudpp, HPTS, and quantum dots or rhodamine B. Further, "Analytical Chimica Acta 606 (2008) pp. 223-229" discloses a technique of detecting temperature and dissolved oxygen concentration using quantum dots and Rudpp, but it concerns the immobilization of quantum dots and Rudpp in adjacent areas on a single thin membrane (See FIGS. 1 and 2.1. Materials therein), which is completely different from making a homogeneous mixture and following immobilization of the mixture.

SUMMARY OF THE INVENTION

The present inventors constructed an optical sensing membrane by mixing Rudpp, HPTS, and quantum dots or rhodamine B, for detecting dissolved oxygen concentration, pH and temperature, respectively, forming a homogenous solution from the mixture, and applying the solution on a support. Further, the present inventors confirmed that the optical sensing membrane could simultaneously detect two or more parameters of dissolved oxygen concentration, pH and temperature, effectively and thus completed the present invention.

Therefore, an object of the present invention is to provide an optical sensing membrane, which can simultaneously detect two or more parameters of dissolved oxygen concentration, pH and temperature effectively.

Another object of the present invention is to provide an optical detection device including the optical sensing membrane.

Still another object of the present invention is to provide an optical detection method using the optical detection device.

One aspect of the present invention relates to an optical sensing membrane for simultaneous detection of two or more parameters of dissolved oxygen concentration, pH and temperature, comprising a support, and a mixture of two or more fluorescent dyes selected from the group consisting of Rudpp; HPTS; and quantum dots or rhodamine B, immobilized on the support.

Another aspect of the present invention relates to a device for simultaneous detection of two or more parameters of dissolved oxygen concentration, pH and temperature, which comprises the optical sensing membrane.

Still another aspect of the present invention relates to a method for simultaneous detection of two or more parameters of dissolved oxygen concentration, pH and temperature, which comprises optically detecting two or more parameters of dissolved oxygen concentration, pH and temperature of an analyte, simultaneously.

DESCRIPTION OF SPECIFIC EMBODIMENTS

Figure 1:
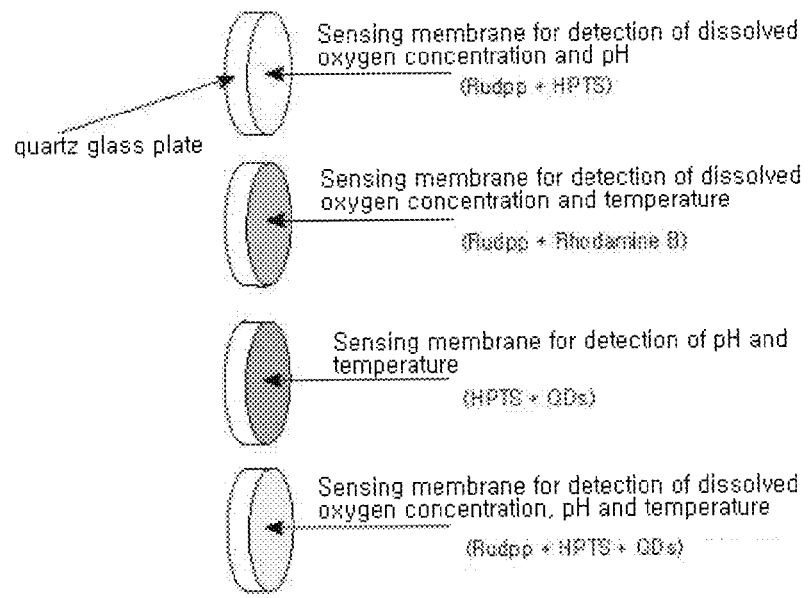
FIG. 1 shows an optical sensing membrane for simultaneous detection, constructed by spreading fluorescent dyes immobilized in a sol-gel solution onto a quartz glass plate.
Figure 2:
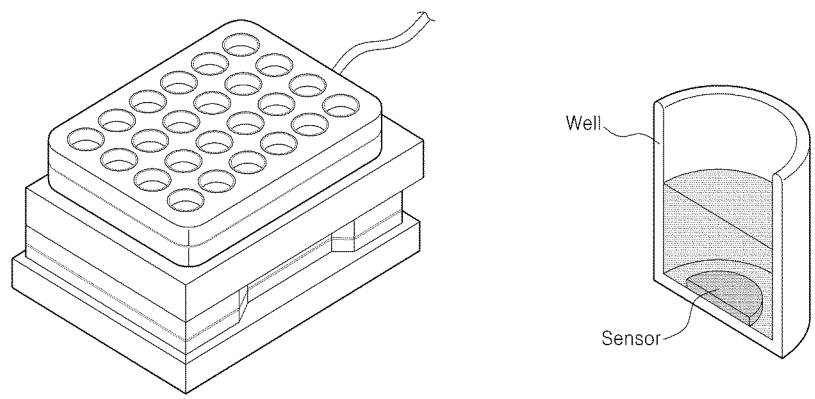
FIG. 2 shows a micro-bioreactor for monitoring constructed by spreading fluorescent dyes immobilized in a sol-gel solution onto a 24-well microtiter pate.

The advantages, features and aspects of the invention will become apparent from the following description of the embodiments with reference to the accompanying drawings, which is set forth hereinafter.

Hereinafter, the present invention will be described in detail.

First, the present invention is characterized in that Rudpp, HPTS and quantum dots or rhodamine B are used to detect dissolved oxygen concentration, pH and temperature, respectively.

Further, the present invention is characterized in that an optical sensing membrane is constructed by intimately mixing two or three of the fluorescent dyes, and then, immobilizing the mixture on a support, which is clearly distinguishable from the prior arts.

A mixing ratio of the three fluorescent dyes constitutes another feature of the present invention. Preferably, a weight ratio of Rudpp:HPTS:quantum dots is in the range of 0.5~1.5: 0.5~1.5:15~25, or a weight ratio of Rudpp:HPTS:rhodamine B is in the range of 0.5~1.5:0.5~1.5:0.0001~0.001. More preferably, a weight ratio of Rudpp:HPTS:quantum dots is in the range of 0.8~1.2:0.8~1.2:18~22, or a weight ratio of Rudpp:HPTS:rhodamine B is in the range of 0.8~1.2:0.8~1.2: 0.0003~0.0007. In a specific embodiment, Rudpp is used at 1~10 mg/ml, preferably 2~5 mg/ml, most preferably 5 mg/ml, HPTS is used at 1~10 mg/ml, preferably 2~7 mg/ml, most preferably 5.2 mg/ml, quantum dots are used at 1~200 mg/ml, preferably 10~100 mg/ml, most preferably 100 mg/ml, or rhodamine B is used at 0.1~10 µg/ml, preferably 1~5 µg/ml, most preferably 2.4 µg/ml. This is because dissolved oxygen concentration, pH and temperature can be effectively detected simultaneously within the above range of ratio.

According to the present invention, it is preferable to adsorb one or more of Rudpp, HPTS, quantum dots and rhodamine B onto an adsorbent prior to use. The adsorbent that can be used in the present invention includes any one known in the art, for example, silica gel, organically-modified silicate (e.g., Ormosil beads) and poly(styrene-block-vinylpyrrolidone) beads. The adsorption of fluorescent dyes enables prevention of fluorescence peak shift and so efficient detection.

Though any of those known in the art can be used as a support for the optical sensing membrane according to the present invention, a quartz glass plate, a glass plate and a transparent polymer such as polystyrene, or a microtiter plate can be more preferably used.

Though any methods known in the art can be used without limitation to immobilize the mixed fluorescent dyes on the support, for example, sol-gel solution, hydrogel, cellulose or derivatives thereof (e.g., alkyl cellulose, particularly $C_{1-6}$ alkyl cellulose, more particularly ethyl cellulose) can be used, and the sol-gel solution can be more preferably used. Since the immobilization of the fluorescent dyes using the sol-gel solution have been known in the art, it can be carried out in accordance with the conventional process known in the art. In particular, in the present invention, methyltrimethoxy silane (MTMS) can be used as an agent for forming a sol-gel, acetone used as a solvent, and hydrochloric acid used as an acid catalyst for the sol-gel condensation reaction. For example, it is preferable to use the sol-gel solution containing MTMS, acetone, water and 30~40 weight % hydrochloric acid in the volume ratio of 200~250:80~120:30~50:1. This is because the ratio can enhance the immobilization efficiency of the mixed fluorescent dyes. More specifically, the sol-gel solution contains MTMS of 3.97 ml, acetone of 1.84 ml, water of 0.72 ml and 35 weight % hydrochloric acid of 18 µl. In a specific embodiment of the present invention, MTMS of 3.97 ml, acetone of 1.84 ml, distilled water of 0.72 ml and 35 weight % hydrochloric acid of 18 µl are stirred for 2~5 hours, particularly 3 hours to be matured, the fluorescent dyes are added thereto, and then, the mixture is treated with ultrasonication for 5~20 minutes, and particularly 10 minutes, to give a homogeneous solution. The mixed fluorescent dye solution is applied onto a support, for example a quartz glass plate or each well of a multi-well (e.g., 24-well) microtiter plate, and then, dried for 12~48 hours, particularly 24 hours at a temperature of 15~30° C., particularly at room temperature and then at a temperature of 50~70° C., particularly at 60° C., to construct an optical sensing membrane.

The optical sensing membrane according to the present invention can be used as an optical fiber sensor by applying it to an optical fiber probe, and the multi-well microtiter plate having the optical sensing membrane coated thereon can be used as a multi-channel micro-bioreactor for monitoring.

Hereinafter, the present invention will be described with reference to the following examples, which are provided only for the better understanding of the present invention, but should not be construed to limit the scope of the present invention in any manner.

PREPARATION EXAMPLE

Preparation of a Sol-Gel for Immobilization of Fluorescent Dyes

MTMS was used as an agent for forming a sol-gel, 99% acetone used as a solvent, and 35% HCl used as a catalyst. MTMS, acetone, water and HCl were mixed at the ratio of 3.97 ml:1.84 ml:0.72 ml:18 µl, and then, vigorously stirred for 3 hours to form the sol-gel solution.

Example 1

Construction of an Optical Sensing Membrane for Simultaneous Detection of Dissolved Oxygen Concentration and pH To construct an optical sensing membrane for simultaneous detection of dissolved oxygen concentration and pH, Rudpp of 5 mg/ml and HPTS of 5.2 mg/ml were mixed with the sol-gel obtained from the preparation example to prepare a sensing membrane solution. Rudpp had been adsorbed onto a silica gel. Specifically, Rudpp of 0.6 g had been introduced to chloroform ($CHCl_3$) of 12 ml, and a silica gel of 2 g added thereto. The mixture had been stirred for 24 hours, filtered through a filter paper (Whatman), washed 3 times with triple distilled water, and then, dried. The prepared sensing membrane solution of 20 µl was dropped on the surface of a quartz glass plate and then dried for one day in the air. In order to make the surface of the sensing membrane smooth, it was further dried at a temperature of 60° C. for one day to construct the sensing membrane.

Example 2

Construction of Optical Sensing Membrane for Simultaneous Detection of Dissolved Oxygen Concentration and Temperature To construct an optical sensing membrane for simultaneous detection of dissolved oxygen concentration and temperature, Rudpp of 5 mg/ml and rhodamine B of 2.4 μg/ml were mixed with the sol-gel solution obtained from the preparation example to prepare a sensing membrane solution. The prepared sensing membrane solution of 20 μl was dropped on the surface of a quartz glass plate and then dried for one day in the air. In order to make the surface of the sensing membrane smooth, it was further dried at a temperature of 60° C. for one day to construct the sensing membrane.

Example 3

Construction of an Optical Sensing Membrane for Simultaneous Detection of pH and Temperature To construct an optical sensing membrane for simultaneous detection of pH and temperature, HPTS of 5.2 mg/ml and QDs of 100 mg/ml were mixed with the sol-gel solution obtained from the preparation example to prepare a sensing membrane solution. The prepared sensing membrane solution of 20 μl was dropped on the surface of a quartz glass plate and then dried for one day in the air. In order to make the surface of the sensing membrane smooth, it was further dried at a temperature of 60° C. for one day to construct the sensing membrane.

Example 4

Construction of an Optical Sensing Membrane for Simultaneous Detection of Dissolved Oxygen Concentration, pH and Temperature To construct an optical sensing membrane for simultaneous detection of dissolved oxygen concentration, pH and temperature, Rudpp of 5 mg/ml, HPTS of 5.2 mg/ml and rhodamine B of 2.4 μg/ml were mixed with the sol-gel solution obtained from the preparation example to prepare a sensing membrane solution. The prepared sensing membrane solution of 20 μl was dropped on the surface of a quartz glass plate and then dried for one day in the air. In order to make the surface of the sensing membrane smooth, it was further dried at a temperature of 60° C. for one day to construct the sensing membrane.

Example 5

Construction of a Multi-Channel 24-Well Micro-bioreactor for Monitoring

The sensing membrane solution of 20 μl prepared in accordance with Examples 1 to 4 was dropped on the bottom of a 24-well microtiter plate, and then, dried for one day in the air. In order to make the surface of the sensing membrane smooth, it was further dried at a temperature of 60° C. for one day to construct the multi-channel 24-well micro-bioreactor.

Experimental Example

Confirmation of the Simultaneous Detectability of Two or More Parameters of Dissolved Oxygen Concentration, pH and Temperature In order to confirm the simultaneous detectability of the sensing membrane according to Examples 1 and 3 with a fluorescent multi-analyzer (Saphire$^2$, TECAN Co., Austria), triple distilled water of 100% dissolved oxygen concentration and 40 g/l sodium sulfite of 0% dissolved oxygen concentration were injected at an amount of 1 ml into a 24-well plate, and then, fluorescence was measured at an excitation wavelength of 480 nm and an emission wavelength of 600 nm. Then, fluorescence was measured at an excitation wavelength of 410 nm and an emission wavelength of 520 nm, using a phosphate buffer in the range of pH 3~9. Finally, fluorescence was measured at an excitation wavelength of 485 nm and an emission wavelength of 535 nm, while changing the temperature of the phosphate buffer in the range of 25~40° C.

Figure 3:
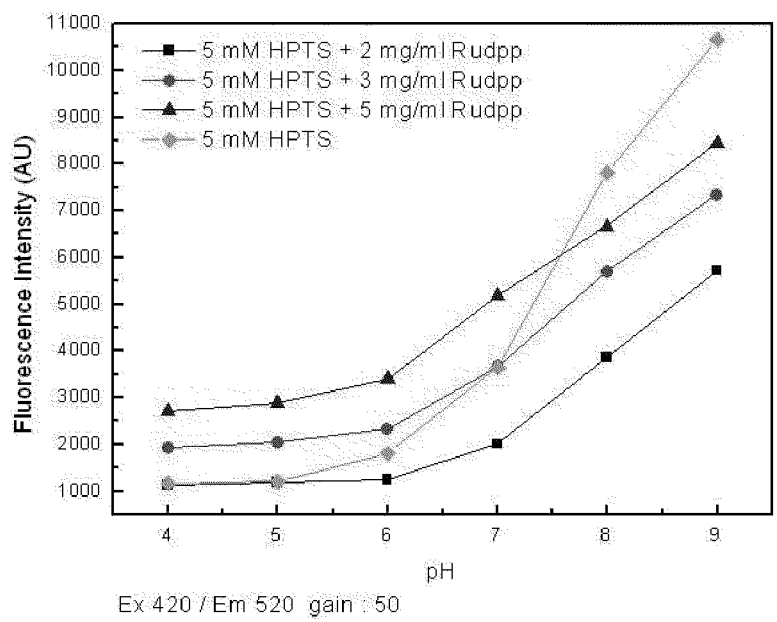
FIG. 3 is a graph showing that the optical sensing membrane in accordance with an embodiment of the present invention can detect dissolved oxygen concentration and pH simultaneously.
Figure 4:
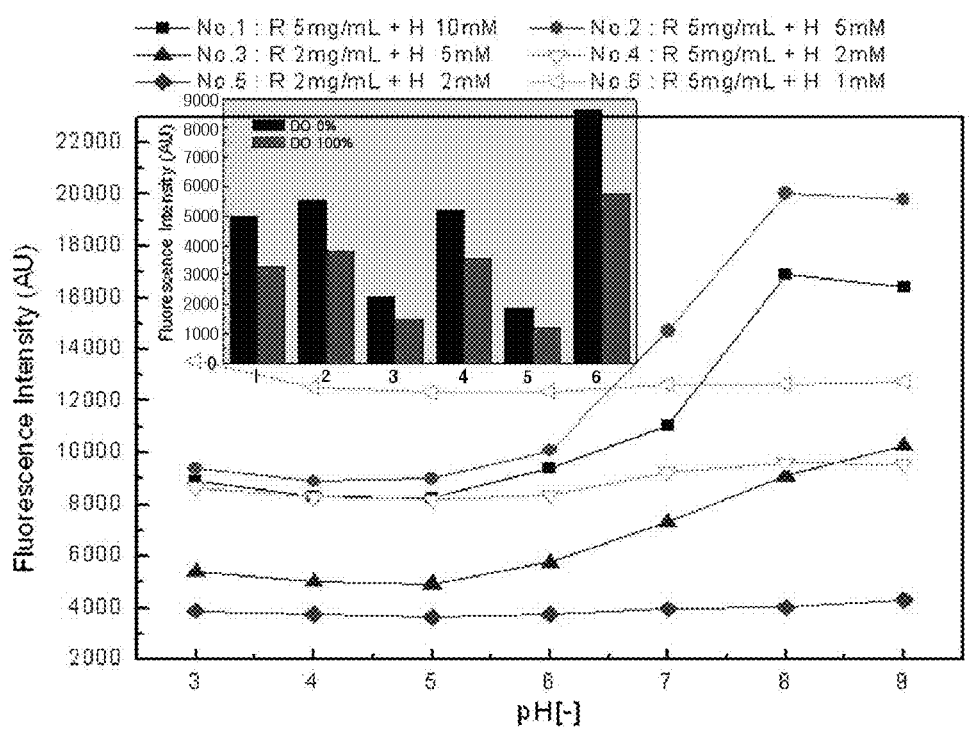
FIG. 4 is a graph showing that the optical sensing membrane in accordance with an embodiment of the present invention can detect dissolved oxygen concentration and pH simultaneously.
Figure 5:
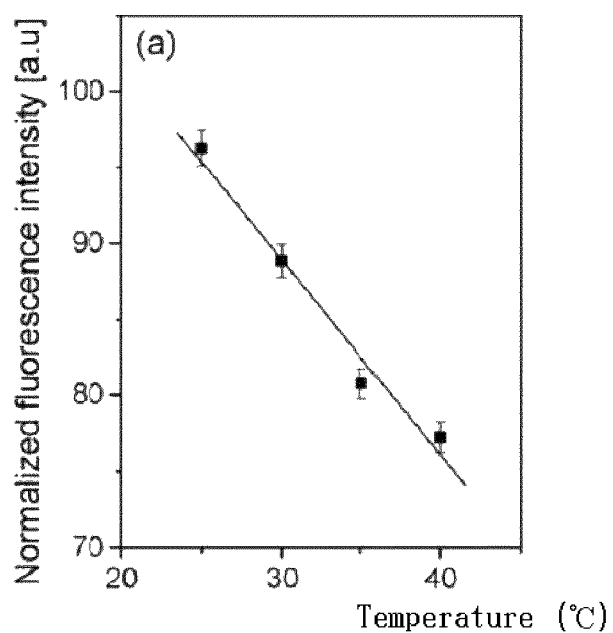
FIG. 5 is a graph showing that the optical sensing membrane in accordance with an embodiment of the present invention can detect dissolved oxygen concentration and temperature simultaneously.

The results are shown in FIGS. 3 to 5. As can be seen from the results shown in the figures, the optical sensing membrane in accordance with the present invention can effectively detect two or more parameters of dissolved oxygen concentration, pH and temperature simultaneously.

Example 6

Construction of an Optical Sensing Membrane for Simultaneous Detection of Two or More Parameters of Dissolved Oxygen Concentration, pH and Temperature The optical sensing membrane was constructed according to substantially the same procedures as in Example 1 to 4, except that the fluorescent dyes were adsorbed onto Ormosil beads, as follows. Teteramethyorthosilicate (TMOS) of 1 ml and dimethyl(dimethylsulfoxide) (DiMe-DMSO) of 1.6 ml were introduced into a vial, stirred for 1 minute, and then, 0.01 mol/l HCl of 2 ml was added thereto. The mixture was dipped into a water bath of 60° C. and then stirred for 3 hours to form an emulsion. After 2 hours, 0.2 ml of the fluorescent dyes dissolved at a concentration of 1.5 g/l in tetrahydrofuran (THF) was added thereto, and the mixture was vigorously stirred to form a homogeneous solution.

Example 7

Construction of an Optical Sensing Membrane for Simultaneous Detection of Two or More Parameters of Dissolved Oxygen Concentration, pH and Temperature The optical sensing membrane was constructed according to substantially the same procedures as in Example 1 to 4, except that the fluorescent dyes were adsorbed onto poly (styrene-block-vinylpyrrolidone) beads, as follows. The poly (styrene-block-vinylpyrrolidone) of 526 mg (containing 200 mg of polymeric beads) was diluted in a mixture of ethanol of 80 mg and water of 40 mg. The fluorescent dye of 3 mg was dissolved in ethanol of 20 ml, and the solution was vigorously stirred while dropping it on the polymeric emulsion. It was concentrated under reduced pressure until ethanol was completely removed, and was diluted with water to make a final volume 20 ml.

Example 8

Construction of an Optical Sensing Membrane for Simultaneous Detection of Two or More Parameters of Dissolved Oxygen Concentration, pH and Temperature The optical sensing membrane was constructed according to substantially the same procedures as in Example 1 to 4, except that a hydrogel was used instead of the sol-gel solution, as follows. The fluorescent dyes and 5% polyurethane hydrogel dissolved in a mixture of ethanol and water (9:1, v/v) were mixed at a weight ratio of 1:40 to construct the optical sensing membrane.

Example 9

Construction of an Optical Sensing Membrane for Simultaneous Detection of two or More Parameters of Dissolved Oxygen Concentration, pH and Temperature The optical sensing membrane was constructed according to substantially the same procedures as in Example 1 to 4, except that ethylcellulose was used instead of the sol-gel solution, as follows. Ethyl cellulose of 200 mg (containing 48% ethoxyl) was dissolved in a mixture of 1.4 ml of 99.5% ethanol and 2 ml of toluene, and the fluorescent dyes of 320 µl were mixed with the cellulose solution of 680 µl to construct the optical sensing membrane.

The optical sensing membrane according to the present invention can be applied to an optical fiber sensor probe, with which a bioreactor is equipped, extremely useful for on-line monitoring of dissolved oxygen concentration, pH and temperature in the reactor. It also enables the monitoring of two or more parameters with a single sensing membrane, and so makes the process simple. Further, the optical sensing membrane can be applied to a multi-well microtiter plate to give a multi-channel multi-well micro-bioreactor for monitoring, optimizing various conditions at one time in a non-invasive manner, thereby to reduce costs and time required for the optimization of production process and so to minimize costs for the development of process.

While the present invention has been described with respect to the specific embodiments, it will be apparent to those skilled in the art that various changes and modifications may be made without departing from the spirit and scope of the invention as defined in the following claims.

What is claimed is:

1. An optical sensing membrane for simultaneous detection of three parameters of dissolved oxygen concentration, pH and temperature, comprising a support, and a homogeneous solution immobilized on the support,
   wherein the homogeneous solution comprises three fluorescent dyes and is made from a homogeneous mixture solution containing: tris(4,7-dipenyl-1,10-phenanthroline) ruthenium (II) complex (Rudpp); 8-hydroxypyrene-1,3,6-trisulfonic acid trisodium salt (HPTS); either Quantum dots (Qds) or rhodamine B, and wherein a weight ratio of Rudpp:HPTS:Quantum dots is 0.5~1.5:0.5~1.5:15~25, or a weight ratio of Rudpp:HPTS:rhodamine B is 0.5~1.5:0.5~1.5:0.0001~0.001; and wherein the homogenous solution immobilized on the support constitutes a single sensor, and the three parameters of dissolved oxygen, pH and temperature are simultaneously measured by means of intensities of a single spectrum from the single sensor.

2. The optical sensing membrane according to claim 1, wherein one or more of Rudpp, HPTS, quantum dots and rhodamine B are adsorbed onto an adsorbent.

3. The optical sensing membrane according to claim 1, wherein the support is a quartz glass plate, a glass plate, a transparent polymer or a multi-well microtiter plate.

4. The optical sensing membrane according to claim 1, wherein the homogeneous solution of fluorescent dyes is immobilized by using a sol-gel, a hydrogel, a cellulose or its derivatives.

5. The optical sensing membrane according to claim 4, wherein the sol-gel comprises methyltrimethoxy silane (MTMS), acetone, water, and 30~40 weight % hydrochloric acid at a volume ratio of 200~250:80~120:30~50:1.

6. A device for simultaneous detection of three parameters of dissolved oxygen concentration, pH and temperature, comprising the optical sensing membrane according to claim 1, which is in the form of an optic fiber sensor or a multi-well microtiter plate.

7. A method for simultaneous detection of three parameters of dissolved oxygen concentration, pH and temperature of a sample, comprising:
   introducing the sample onto the optical sensing membrane according to claim 1; and
   measuring the fluorescence from the optical sensing membrane to detect the dissolved oxygen concentration, pH and temperature.

\* \* \* \* \*